(12) United States Patent
Kourides et al.

(10) Patent No.: US 6,365,127 B1
(45) Date of Patent: *Apr. 2, 2002

(54) ISOLATION OF A GENE ENCODING HUMAN THYROTROPIN BETA SUBUNIT

(75) Inventors: Ione A. Kourides, Forest Hills; Graham Kerr Whitfield, New York, both of NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/516,352

(22) Filed: Mar. 1, 2000

Related U.S. Application Data

(63) Continuation of application No. 08/957,545, filed on Oct. 24, 1997, which is a continuation of application No. 08/006,208, filed on Jan. 19, 1993, now Pat. No. 5,840,566, which is a continuation of application No. 07/671,134, filed on Mar. 18, 1991, now abandoned, which is a continuation of application No. 06/808,004, filed on Dec. 11, 1985, now abandoned.

(51) Int. Cl.$^7$ .......................... A61K 49/00; C07K 14/59; C07H 21/04
(52) U.S. Cl. .......................... 424/9.1; 435/320.1; 435/6; 435/7.1; 530/324; 530/350; 536/23.1; 536/23.5; 536/23.51
(58) Field of Search .......................... 435/320.1, 6, 7.1; 530/324, 350; 424/9.1; 536/23.1, 23.5, 23.51

(56) References Cited

PUBLICATIONS

Birken, Steven and Canfield, Robert E., *J. Biol. Chem.*, vol. 252, No. 15, pp. 5386–5397, 1977.
Boothby, Mark et al., *J. Biol. Chem.*, vol. 256, No. 10, pp. 5121–5127, 1981.
Croyle, Michelle L. and Maurer, Richard A., *DNA*, vol. 3, No. 4, pp. 231–236, 1984.
Fiddes et al., J. Mol. Appl. Genet. 1:3 3–18, 1981.
Gurr, James A., et al., *Proc. Natl. Acad. Sci.*, vol. 80, pp. 2122–2126, 1983.
Hayashikaki et al., *FEBS Lett.* 188: 394–400, 1985.
Kaufman et al., *Molecular and Cell. Bio.* 2:1304–1309, 1982.
Keutmann, Henry T. and Williams, Roberta M., *J. Biol. Chem*, vol. 252, No. 15, pp. 5393–5397, 1977.
Keutmann, Henry T., et al., *Biochem. Biophys. Res. Commun.*, vol. 90, No. 3, pp. 842–848, 1979.
Kourides, Ione A., et al., *Recent Progress in Hormone Research*, vol. 40, pp. 79–120, 1984.
Maniatis et al., Molecular Cloning: A Laboratory Manual, Cold Springs Harbor Literature, pp. 270–247, 1982.
Maurer et al., *J. Biol. Chem.* vol., 259:3024–3027, 1984.
Maurer, Richard A., et al., *J. Biol. Chem.*, vol. 259, No. 8, pp. 5024–5027, 1983.
Morgan, Francis, J., et al., *J. Bio. Chem.*, vol. 20, No. 13, pp. 5247–5248, 1975.
Pierce, John G., *Endocrinology*, vol. 89, pp. 1331–1344, 1971.
Pierce, John G. and Parsons, Thomas F., *Ann. Rev. Biochem.*, vol. 50, pp. 465–495, 1981.
Policastro, Paul, et al., *J. Biol. Chem.*, vol. 258, No. 19, pp. 11492–11499, 1983.
Sairam et al. Can. J. Biochemistry 55: 755–760, 1977.
Shome, B. And A.F. Parlow (1973). *J. Clin. Endocrinol. Metab.* 36:618–621.
Suggs et al. *Proc. Nat'l Acad,.* Sci. 78: 6613–7, 1981.
Talmadge, K., et al. (1983). The human genome contains seven genes for the β–subunit of chorionic gonadotropin but only one gene for the β–subunit of luteinizing hormone. 2: 281–289.
Vamkapoulos et al., *Proc. Nat'l Acad. Sci.* 77; 3149–53, 1980.

*Primary Examiner*—David Guzo
(74) *Attorney, Agent, or Firm*—John P. White; Cooper & Dunham LLP

(57) ABSTRACT

The gene expressing the beta subunit of human thyroid stimulating hormone has been isolated. The gene has been incorporated into plasmid pBR322. Vectors can be used to transform cells which in turn produce pure beta subunits. The beta subunits can then be combined with the alpha subunit of human glycoprotein hormones to produce pure thyroid stimulating hormone.

9 Claims, 3 Drawing Sheets

FIGURE 2

```
CTTTTTCTTGGTTCTTGCCCTTTCTGATTTTAACAAATAGGTTCTTTAATTTATCTTGATTTAGC

-20
                        met thr ala leu phe leu met ser met leu phe gly
                        ATG ACT GCT CTC TTT CTG ATG TCC ATG CTT TTT GGC
              10                                              -10
leu ala cys gly gln ala met ser phe cys ile pro thr glu tyr thr met his ile glu arg arg glu cys ala tyr cys  leu thr ile
CTT GCA TGT GGG CAA GCG ATG TCT TTT TGT ATT CCA ACT GAG TAT ACA ATG CAC ATC GAA AGG AGA GAG TGT GCT TAT TGC CTA ACC ATC
                    30                                                                      20
asn thr thr ile cys ala gly tyr cys met thr arg
AAC ACC ACC ATC TGT GCT GGA TAT TGT ATG ACA CGG  GTATGTAGTTCATGTCACTTCTTTTTGGCTGTAAATTATATAAGCCCTGAAGAAGTCCATTCCTATATAGAA AGGAAATGAAATAAATCACAA - - - - - - - - - - - - - 150-200 bp - - - - - - - - - - - - - -

AATTCAACGTGGTAAGTTGGTATTGGAGAATGGGGCTAAGCAATTCTTCGCAGTGTATTGTGATGAAGGAATAAGTGAATTTATTTTATGTTTCTATTATCTATATGTTTCC 35                                                    50
                        asp ile asn gly lys leu phe leu pro lys tyr ala leu ser gln asp val cys
                        GAT ATC AAT GGC AAA CTG TTT CTT CCC AAA TAT GCT CTG TCC CAG GAT GTT TGC
TAAAGTCCTCACATTATGCTCTCTTTCTGTTCTTTCCCCAG                                              40                                      80
                                                                                                                      pro val ala leu ser
                                                                                                                      CCT GTT GCT TTA AGC
thr tyr arg asp phe ile tyr arg thr val glu ile pro gly cys pro leu his val ala ile lys thr asn tyr cys thr lys  pro gln lys ser tyr
ACA TAT AGA GAC TTC ATC TAT AGG ACT GTA GAA ATA CCA GGA TGC CCA CTC CAT GTT GCT ATC AAG ACA AAC TAC TGT ACC AAA CCT CAG AAG TCT TAT
          60                                          70                                    100                           110 cys lys cys gly lys cys ser asp tyr asp cys ile his glu ala ile lys thr asn tyr cys thr lys pro gln lys ser tyr
TGT AAG TGT GGC AAG TGC AGT GAC TAT GAC TGC ATA CAT GAA GCC ATC AAG ACA AAC TAC TGT ACC AAA CCT CAG AAG TCT TAT
                90                                  100                                              110
                                                                                                              118
leu val gly phe ser val OC
CTG GTA GGA TTT TCT GTC TAA TAGTGAATAATTTGCAATTTGGTTAAATGTGCTTGCCTGAAATAAAGCTAATAAAAATATTATGTTTCACATTATCTTCTGTTCATTTGAG
```

ISOLATION OF A GENE ENCODING HUMAN THYROTROPIN BETA SUBUNIT

This application is a continuation of U.S. Ser. No. 08/957,545, filed Oct. 24, 1997, a continuation of Ser. No. 08/006,208, filed Jan. 19, 1993, now U.S. Pat. No. 5,840,566, issued Nov. 24, 1998, a continuation of Ser. No. 07/671,134, filed Mar. 18, 1991, now abandoned a continuation of Ser. No. 06/808,004, filed Dec. 11, 1985, now abandoned the contents of which are hereby incorporated into this application by reference.

FIELD OF THE INVENTION

This invention relates to the human thyroid stimulating hormone Beta chain or subunit (hTSH-β), and the gene producing it. Further, the invention relates to applications of this gene.

BACKGROUND AND PRIOR ART

The thyroid stimulating hormone (TSH) is a member of a family of glycoprotein hormones which includes the gonadotropins, luteinizing hormone, follicle stimulating hormone, and chorionic gonadotropin. See, e.g., Kourides et. al., *Rec. Prog. Hormone Res.* 40:79–120 (1984).

Each of the hormones listed supra has been found to consist of two dissimilar, noncovalently bound subunits, alpha and beta.

In an individual species, the alpha subunit for all of the hormones listed has been found to be identical, while the beta unit is different. It is the beta subunit that gives biologic and immunologic specificity to the hormones. Again, in the same species, there are areas of strong homology among the beta subunits.

Pierce, *Endocrinology* 89:1331 (1971), and Pierce et. al., *Ann. Rev. Biochem.* 50:465 (1981), show that any alpha subunit can be combined with a beta subunit to give a complete hormone. Shome, et. al., *J. Clin. Endocrin. Metab.* 36:618 (1983); Morgan, et. al., *J. Biol. Chem.* 250:5247 (1975); Birken, et. al., *J. Biol. Chem.* 252:5386 (1977) and Keutmann, et. al., *J. Biol. Chem.* 252:5393 (1977), and *Biochem. Biophys. Res. Commun.* 90:842 (1979), have shown that the beta subunits of chorionic gonadotropin and luteinizing hormone are most closely related, with amino acid sequence homology of 82%. Other beta subunits have lower amino acid sequence homolgies, in the range of 25–40%. Pierce, et. al., (1981) supra.

A single gene coding for the alpha subunit of human glycoprotein hormones has been isolated. Fiddes, et. al., *J. Mol. Appl. Genet.* 1:3 (1981); Boothby, et. al., *J. Biol. Chem.* 256:5121 (1981). Additionally, seven human chorionic gonadotropin beta subunit genes and one human luteinizing hormone beta subunit gene have been isolated. Talmadge, et. al., *DNA* 2:281 (1983); Policastro, et. al., *J. Biol. Chem.* 258:11492 (1983). These beta subunit genes are all highly homologous and are linked on a fragment of human chromosome 19, less than 50 kilobases long.

With respect to the beta subunit of human thyroid stimulating hormone, it has not been possible, until now, to obtain the gene expressing this subunit. This is in spite of the fact that mouse TSH-beta subunit cDNA has been synthesized and cloned and the mouse gene isolated. The gene obtained has been characterized following cross-species hybridization experiments. Gurr, et. al., *Proc. Natl. Acad. Sci.* 80:2122 (1983); Kourides, et. al., supra (1984). Rat and bovine TSH beta subunit cDNA have also been cloned. Croyle, et. al., *DNA* 3:231 (1984); Maurer, et. al., *J. Biol. Chem.* 259:5024 (1984). Now, using mouse and bovine cDNA which have been cloned, the gene expressing human thyroid stimulating hormone beta chains has been obtained.

Usually, in obtaining a desired gene, the practice is to isolate the mRNA produced by transcription of the desired gene. Once this is obtained, cDNA can be synthesized and used as a hybridization probe to isolate the complementary gene. The methods for doing this are well known to the art. In the case of the beta subunit of human TSH, this method has proven to be unworkable. Undegraded mRNA has not been available from human pituitary glands, post mortem or post surgery.

The difficulties involved, however, have now been overcome. By relying on cDNA of different species, i.e., mouse and bovine, it has been and now is possible to obtain the gene expressing the beta subunit of human thyroid stimulating hormone.

BRIEF DESCRIPTION OF THE FIGURES

FIG. 2 is the nucleotide sequence (SEQ ID NOS: 1 and 2) of protein coding exons of hTSH-β, and the amino acid sequence (SEQ ID NOS: 3 and 4) deduced therefrom.

DETAILED DESCRIPTION OF PREFERRED EMBODIMENTS

A human genomic library, obtained by partial digestion of white blood cell DNA with the restriction endonuclease EcoRI, followed by insertion of the partially digested genome into phage λCharon 4A was used. This library was screened using probes consisting of plasmids containing cDNA for bovine and murine TSH-β. See, Benton, et. al., *Science* 196:180 (1977), for the method used. The plasmid probes had been labelled with $[\alpha^{32}P]$-dCTP, via nick translation, according to the method of Rigby, et. al., *J. Mol. Biol.* 113:237 (1977).

Figure 1:
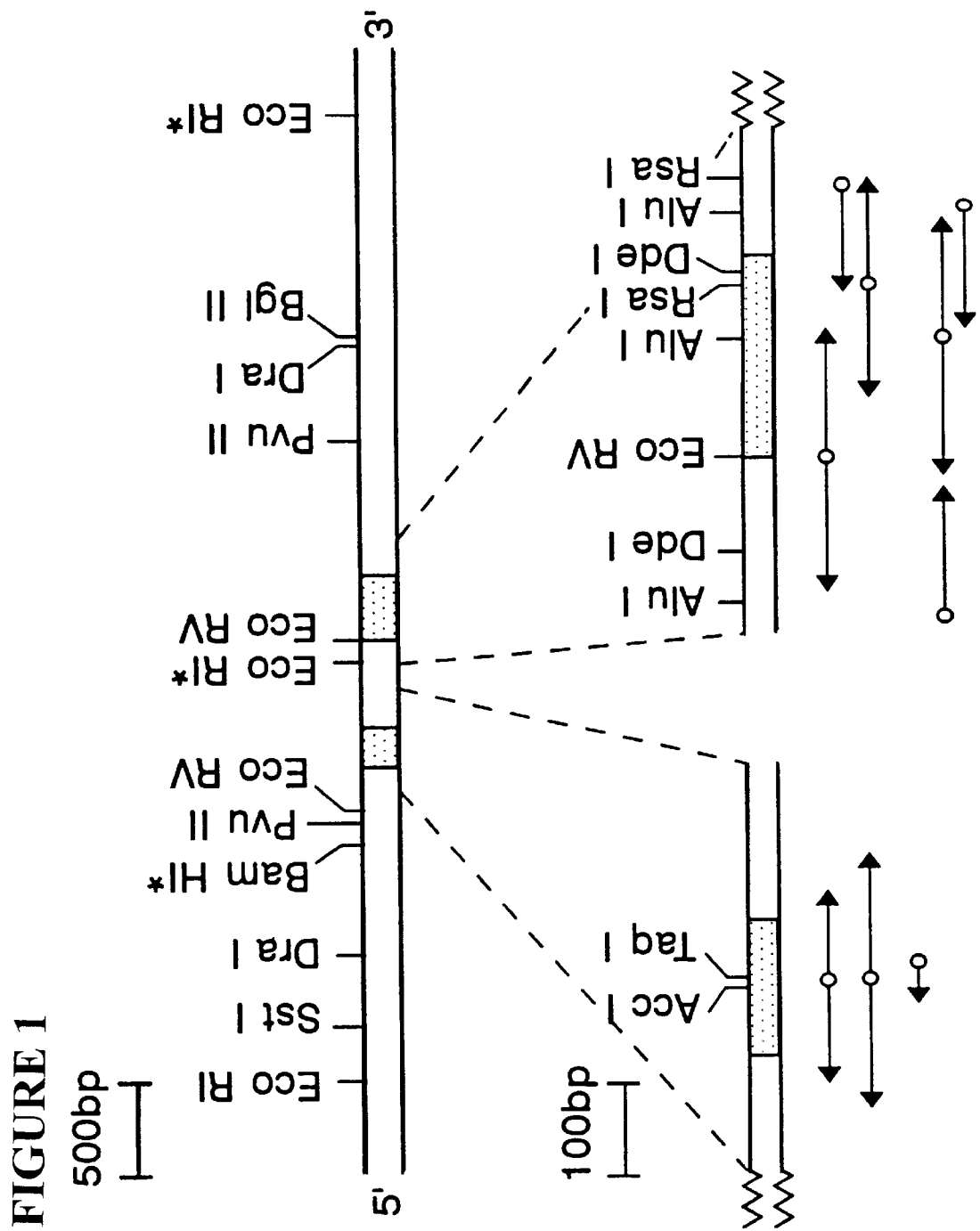
FIG. 1 is a map of the restriction enzyme sites of cloned hTSH-β.

The screening procedure described by Benton & Davis was used to examine $3\times10^5$ phage and yielded 3 phage which hybridized to the mouse and bovine cDNAs. The 3 phage were similar and the restriction map is presented in FIG. 1.

Two digested, hybridizing fragments were subcloned into plasmid pBR322, and the new plasmids were used to transform *E. coli* strain HB101. Hanahan *J. Mol. Biol.* 166:557 (1983). The fragments measured 0.9 Kb (BamHI-EcoRI) and 3.6 Kb (EcoRI). These fragments are adjacent, and are indicated by asterisks in FIG. 1. These fragments were themselves mapped and partially sequenced. Maxam et al, *Methods Enzymol.* 65:499 (1980). The determined nucleotide sequence yielded a deduced amino acid sequence which unambiguously identified the gene as expressing human TSH-β.

The plasmids and transformed *E. coli* cells have been deposited at the Sloan-Kettering Institute for Cancer Research, and are available to one determined by the Commissioner to be entitled to these. Further, these plasmids and cell lines have been deposited on Jan. 15, 1987 in *Escherichia coli* cells, DH1 harboring pBR322 plasmid containing a 3.6 kb h-TSH-β gene fragment, and *Escherichia coli* cells harboring pBR322 plasmid containing a 0.9 kb h-TSH-β gene fragment, pursuant to the Budapest Treaty on International Recognition of the Deposit of Microorganisms for the Purposes of Patent Procedure with the Patent Culture Depository of the American Type Culture Collection (ATCC), now located at 10801 University Blvd., Manassas, Va. 20110-2209, U.S.A. under ATCC Designation Nos. 67297 and 67298, respectively.

FIG. 2 displays the nucleotide sequence of both the 0.9 and 3.6 Kb regions, together with the amino acid sequence for which these code. It will be seen that the 0.9 Kb region contains an exon encoding expresses a 20 amino acid hydrophobic signal followed by 34 amino acids of secretory TSH-β. The 3.6 Kb fragment contained an exon expressing the remaining 84 amino acids of TSH-β. Separating the two exons was an intron of about 400–450 base pairs.

Figure 3:
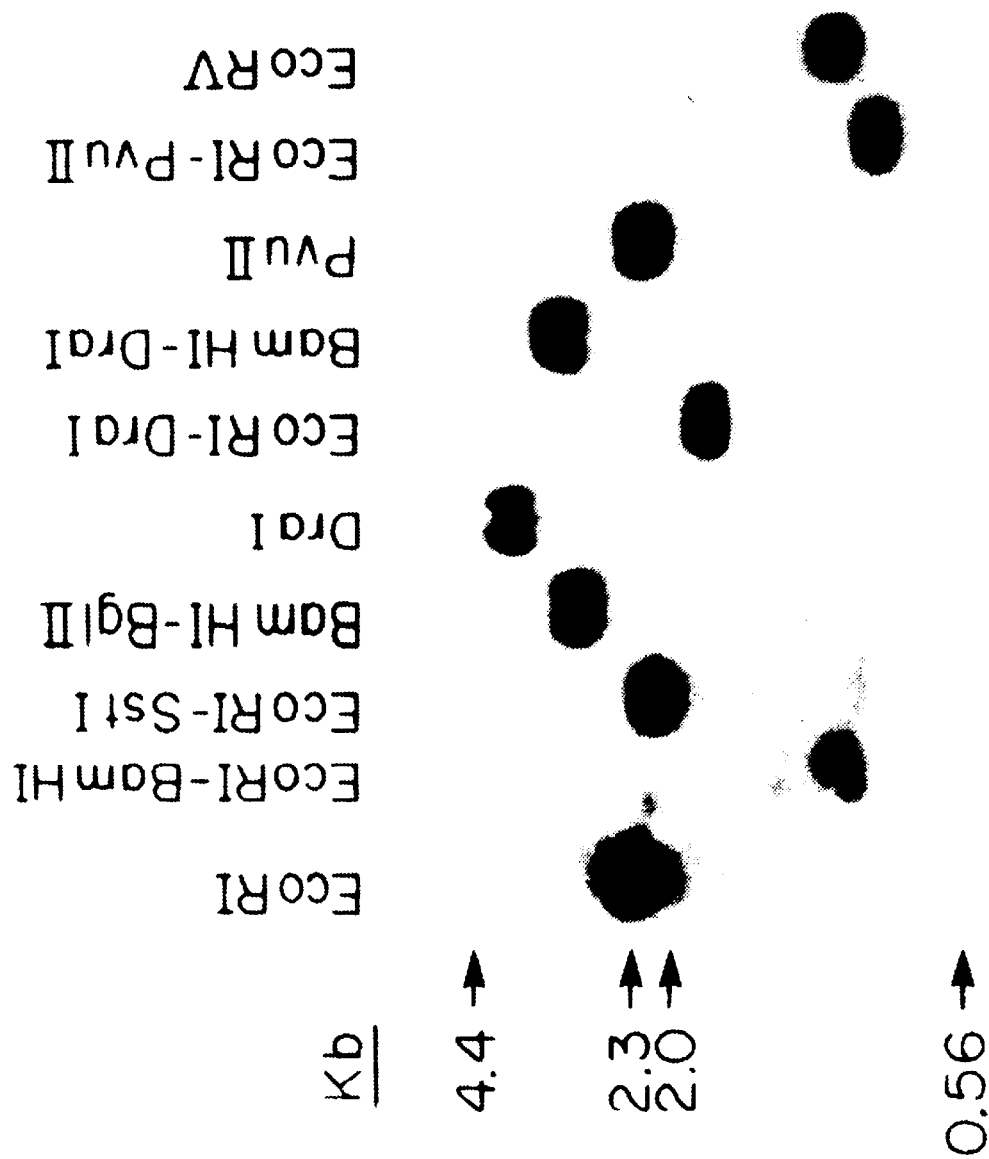
FIG. 3 shows the results of restriction analysis of hTSH-B gene in human genomic DNA.

The BamHI-EcoRI 0.9 Kb fragment was used as a probe to investigate the structure of the human TSH-β gene in total genomic DNA. The results of these experiments are displayed in FIG. 3. Briefly, samples of endonuclease digested term placental DNA were resolved on a 1% agarose gel, and then transferred to nitrocellulose filters by the method of Southern, *J. Mol. Biol.,* 98:503 (1975). Following transfer, a $^{32}$P labelled probe, comprising the 0.9 Kb fragment, was added to the filter bound DNA. Each digest of the human DNA yielded only a single hybridizing band whose size agreed with that obtained from the phage. From this, it may be concluded that human TSH-β is expressed by one gene. See FIG. 3.

The amino acid sequence deduced from the nucleotide sequence agrees with the published sequence of human TSH-β gene, with exceptions as follows: residue 8 and 9 are found to be threonine-methionine, a transposition compared to Sairam, et. al., *Can. J. Biochem.* 55:755 (1977); residue 89 is aspargine, as compared to aspartate in Sairam. Also, the derived sequence described herein contains 6 additional amino acids at the C-terminus as compared to the published sequence.

The human gene for TSH-β subunit codes for a peptide of 118 amino acids, plus an N-terminal leader sequence of 20 amino acids. The 20 amino acid leader sequence is characteristic of β-subunits of the glycoprotein hormones. See, e.g., Talmadge, et. al., *Nature* 307:37 (1984); Jameson, et. al., *J. Biol. Chem.* 259:15474 (1984). The number of amino acids in the peptide (118) is identical to the number found in mouse, rat and cow TSH-β subunits. When compared to corresponding regions of mouse, bovine, and rat TSH cDNA as presented by Gurr, et. al., *Proc. Natl. Acad. Sci.* 80:2122 (1983); Croyle, et. al., *DNA* 3:231 (1984) and Maurer, et. al., *J. Biol. Chem.* 259:5024 (1984), the protein encoding regions of the human gene display homology of 84%, 90%, and 83%, respectively.

Study of this gene reveals that the intron occurs between amino acids 34 and 35 of the secretory protein. This is a conserved position for the 3'-ward introns occurring also in human and rat luteinizing hormone β subunits, Talmadge, et. al., supra (1984); Jameson, et. al., supra (1984).

Due to the difficulties in obtaining undegraded human TSH-β mRNA, it was difficult to identify 5' and 3' untranslated regions of the gene. It is known that the sequence immediately downstream of the stop codon is strongly homologous to 3'-untranslated regions of mouse, bovine and rat TSH-β cDNAs. It is therefore likely that the 3' untranslated region is present in the clone. In contrast, sequences upstream from the first methionine codon bear no homology to the 5'-untranslated regions of other species. This lends support to the hypothesis that this region is an intron.

While the embodiment set forth supra, describes plasmids prepared using pBR322, one skilled in the art will appreciate that there are many plasmids which can be used in subcloning. These plasmids may be naturally occurring or synthesized in the laboratory.

Further, one skilled in the art will appreciate the applicability of this invention to the transformation of cells, both prokaryotic and eukaryotic. As has been described, supra, *E. coli* strain HB101 was transformed by plasmid pBR322 which has been subcloned with fragments of the human TSH-β gene. Using similar mechanisms, *E. coli* and other prokaryotes may be so transformed.

Additionally, the state of the art is such that eukaryotic cells may be transformed by appropriate vectors such as viruses containing the human TSH-β gene. This allows for production of this protein, in glycosylated form, in vitro. By amplification means known to the art, it is also possible to increase the production of the protein to high levels.

Perhaps the most interesting use of the isolated gene is in diagnostics. Various endocrine disorders are characterized by overproduction or underproduction of hormones, including thyroid stimulating hormone. One could administer hTSH made by recombinant DNA technology to humans in order to determine whether thyroid gland failure is due to primary thyroid disease or central pituitary or hypothalamic disease.

The terms and expressions which have been employed are used as terms of description and not of limitation, and there is no intention in the use of such terms and expressions of excluding any equivalents of the features shown and described or portions thereof; it being recognized that various modifications are possible within the scope of the invention.

What is claimed is:

1. A thyroid stimulating hormone beta chain produced by a cell transformed with a vector comprising a DNA sequence encoding the beta subunit of human thyroid stimulating hormone, wherein the DNA sequence comprises the following sequence:
   (a) a first sequence ATG ACT GCT CTC TTT CTG ATG TCC ATG CTT TTT GGC CTT GCA TGT GGG CAA GCG ATG TCT TTT TGT ATT CCA ACT GAG TAT ACA ATG CAC ATC GAA AGG AGA GAG TGT GCT TAT TGC CTA ACC ATC AAC ACC ACC ATC TGT GCT GGA TAT TGT ATG ACA CGG;
   (b) a second sequence of about 400–450 nucleotides following the first sequence; and
   (c) a third sequence GAT ATC AAT GGC AAA CTG TTT CTT CCC AAA TAT GCT CTG TCC CAG GAT GTT TGC ACA TAT AGA GAC TTC ATC TAC AGG ACT GTA GAA ATA CCA GGA TGC CCA CTC CAT GTT GCT CCC TAT TTT TCC TAT CCT GTT GCT TTA AGC TGT AAG TGT GGC AAG TGC AAT ACT GAC TAT AGT GAC TGC ATA CAT GAA GCC ATC AAG ACA AAC TAC TGT ACC AAA CCT CAG AAG TCT TAT CTG GTA GGA TTT TCT GTC TAA following the second sequence.

2. A method of determining the cause of a thyroid gland failure in a subject comprising: administering to the subject human thyroid stimulating hormone prepared by recombinant DNA technology; and determining whether such administration results in a change in the activity of said subject's thyroid gland, a change indicating that the thyroid gland failure results from central pituitary disease, and no change indicating primary thyroid failure.

3. Substantially pure human thyroid stimulating hormone comprising a beta subunit prepared by recombinant DNA technology and having the amino acid sequence set forth in SEQ ID NO:3 or SEQ ID NO:4.

4. Substantially pure human thyroid stimulating hormone comprising a beta subunit produced using a plasmid comprising a DNA sequence encoding said subunit, which plasmid is pBR322 and wherein the DNA sequence comprises:
   (a) a first sequence ATG ACT GCT CTC TTT CTG ATG TCC ATG CTT TTT GGC CTT GCA TGT GGG CAA GCG ATG TCT TTT TGT ATT CCA ACT GAG TAT ACA ATG CAC ATC GAA AGG AGA GAG TGT GCT TAT TGC CTA ACC ATC AAC ACC ACC ATC TGT GCT GGA TAT TGT ATG ACA CGG;
   (b) a second sequence of about 400–450 nucleotides following the first sequence; and
   (c) a third sequence GAT ATC AAT GGC AAA CTG TTT CTT CCC AAA TAT GCT CTG TCC CAG GAT GTT TGC ACA TAT AGA GAC TTC ATC TAC AGG ACT GTA GAA ATA CCA GGA TGC CCA CTC CAT GTT GCT CCC TAT TTT TCC TAT CCT GTT GCT TTA AGC TGT AAG TGT GGC AAG TGC AAT ACT GAC TAT AGT GAC TGC ATA CAT GAA GCC ATC AAG ACA AAC TAC TGT ACC AAA CCT CAG AAG TCT TAT CTG GTA GGA TTT TCT GTC TAA following the second sequence.

5. The substantially pure human thyroid stimulating hormone of claim 4, wherein the plasmid is the pBR322 plasmid having ATCC Designation No. 67297.

6. The substantially pure human thyroid stimulating hormone of claim 4, wherein the plasmid is the pBR322 plasmid having ATCC Designation No. 67298.

7. Substantially pure human thyroid stimulating hormone comprising a beta subunit produced by a vector comprising a DNA sequence encoding said subunit, wherein the DNA sequence comprises:
   (a) a first sequence ATG ACT GCT CTC TTT CTG ATG TCC ATG CTT TTT GGC CTT GCA TGT GGG CAA GCG ATG TCT TTT TGT ATT CCA ACT GAG TAT ACA ATG CAC ATC GAA AGG AGA GAG TGT GCT TAT TGC CTA ACC ATC AAC ACC ACC ATC TGT GCT GGA TAT TGT ATG ACA CGG;

(b) a second sequence of about 400–450 nucleotides following the first sequence; and (c) a third sequence GAT ATC AAT GGC AAA CTG TTT CTT CCC AAA TAT GCT CTG TCC CAG GAT GTT TGC ACA TAT AGA GAC TTC ATC TAC AGG ACT GTA GAA ATA CCA GGA TGC CCA CTC CAT GTT GCT CCC TAT TTT TCC TAT CCT GTT GCT TTA AGC TGT AAG TGT GGC AAG TGC AAT ACT GAC TAT AGT GAC TGC ATA CAT GAA GCC ATC AAG ACA AAC TAC TGT ACC AAA CCT CAG AAG TCT TAT CTG GTA GGA TTT TCT GTC TAA following the second sequence.

8. The substantially pure human thyroid stimulating hormone of claim 4 or 7, wherein the beta subunit-encoding DNA sequence comprises the nucleotide sequence:

ATG ACT GCT CTC TTT CTG ATG TCC ATG CTT TTT GGC CTT GCA TGT GGG CAA GCG ATG TCT TTT TGT ATT CCA ACT GAG TAT ACA ATG CAC ATC GAA AGG AGA GAG TGT GCT TAT TGC CTA ACC ATC AAC ACC ACC ATC TGT GCT GGA TAT TGT ATG ACA CGG.

9. The substantially pure human thyroid stimulating hormone of claim 4 or 7, wherein the beta subunit-encoding DNA sequence comprises the nucleotide sequence:

GAT ATC AAT GGC AAA CTG TTT CTT CCC AAA TAT GCT CTG TCC CAG GAT GTT TGC ACA TAT AGA GAC TTC ATC TAC AGG ACT GTA GAA ATA CCA GGA TGC CCA CTC CAT GTT GCT CCC TAT TTT TCC TAT CCT GTT GCT TTA AGC TGT AAG TGT GGC AAG TGC AAT ACT GAC TAT AGT GAC TGC ATA CAT GAA GCC ATC AAG ACA AAC TAC TGT ACC AAA CCT CAG AAG TCT TAT CTG GTA GGA TTT TCT GTC TAA.

* * * * *

UNITED STATES PATENT AND TRADEMARK OFFICE
CERTIFICATE OF CORRECTION

| | | |
|---|---|---|
| PATENT NO. | : 6,365,127 B1 | Page 1 of 1 |
| APPLICATION NO. | : 09/516352 | |
| DATED | : April 2, 2002 | |
| INVENTOR(S) | : Ione A. Kourides and Graham K. Whitfield | |

It is certified that error appears in the above-identified patent and that said Letters Patent is hereby corrected as shown below:

In the specification at column 1, line 3: Insert

The invention described herein was made in the course of work under Grant No. RO1-CA-23185 from the National Institute of Health. The United States Government has certain rights in this invention.

Signed and Sealed this

Thirteenth Day of May, 2008

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 323
<212> TYPE: DNA
<213> ORGANISM: human
<220> FEATURE:
<221> NAME/KEY: CDS
<222> LOCATION: (70)..(231)

<400> SEQUENCE: 1
```

-continued

```
cttttcttg gtttctttgc cctttctgat tttaacaaat aggttcttta attttatctt      60 tgatttagc atg act gct ctc ttt ctg atg tcc atg ctt ttt ggc ctt gca    111
          Met Thr Ala Leu Phe Leu Met Ser Met Leu Phe Gly Leu Ala
           1               5                  10 tgt ggg caa gcg atg tct ttt tgt att cca act gag tat aca atg cac      159
Cys Gly Gln Ala Met Ser Phe Cys Ile Pro Thr Glu Tyr Thr Met His
 15              20                  25                  30 atc gaa agg aga gag tgt gct tat tgc cta acc atc aac acc acc atc      207
Ile Glu Arg Arg Glu Cys Ala Tyr Cys Leu Thr Ile Asn Thr Thr Ile
             35                  40                  45 tgt gct gga tat tgt atg aca cgg gtatgtagtt catgtcactt cttttggctg     261
Cys Ala Gly Tyr Cys Met Thr Arg
             50 taaattatat aagccctgaa gaagtccatt cctatataga aggaaatga aataaatcac    321 aa                                                                   323

<210> SEQ ID NO 2
<211> LENGTH: 54
<212> TYPE: PRT
<213> ORGANISM: human

<400> SEQUENCE: 2

Met Thr Ala Leu Phe Leu Met Ser Met Leu Phe Gly Leu Ala Cys Gly
 1               5                  10                  15

Gln Ala Met Ser Phe Cys Ile Pro Thr Glu Tyr Thr Met His Ile Glu
             20                  25                  30

Arg Arg Glu Cys Ala Tyr Cys Leu Thr Ile Asn Thr Thr Ile Cys Ala
         35                  40                  45

Gly Tyr Cys Met Thr Arg
     50

<210> SEQ ID NO 3
<211> LENGTH: 511
<212> TYPE: DNA
<213> ORGANISM: human
<220> FEATURE:
<221> NAME/KEY: CDS
<222> LOCATION: (164)..(418)

<400> SEQUENCE: 3
aattcaacgt ggttaagttg gtattggaga atggggctaa gcaattcttt cgcagttgta    60
tttgtgatga aggaatataa gtgaatttat ttttatgttt ctattatcta tatgtttcct   120
aaagtcctgt cacattatgc tctctttct gttctttccc cag gat atc aat ggc     175
                                                Asp Ile Asn Gly
                                                 1 aaa ctg ttt ctt ccc aaa tat gct ctg tcc cag gat gtt tgc aca tat   223
Lys Leu Phe Leu Pro Lys Tyr Ala Leu Ser Gln Asp Val Cys Thr Tyr
 5                  10                  15                  20 aga gac ttc atc tac agg act gta gaa ata cca gga tgc cca ctc cat   271
Arg Asp Phe Ile Tyr Arg Thr Val Glu Ile Pro Gly Cys Pro Leu His
             25                  30                  35 gtt gct ccc tat ttt tcc tat cct gtt gct tta agc tgt aag tgt ggc   319
Val Ala Pro Tyr Phe Ser Tyr Pro Val Ala Leu Ser Cys Lys Cys Gly
             40                  45                  50 aag tgc aat act gac tat agt gac tgc ata cat gaa gcc atc aag aca   367
Lys Cys Asn Thr Asp Tyr Ser Asp Cys Ile His Glu Ala Ile Lys Thr
     55                  60                  65 aac tac tgt acc aaa cct cag aag tct tat ctg gta gga ttt tct gtc   415
```

-continued

```
Asn Tyr Cys Thr Lys Pro Gln Lys Ser Tyr Leu Val Gly Phe Ser Val
    70              75              80 taa tagtgatata atttgcaatt tggttaaatg tgcttgcctg aaataaagct           468
aataaaaata ttatgtttca cattatcttc tgttcatttt gag                     511

<210> SEQ ID NO 4
<211> LENGTH: 84
<212> TYPE: PRT
<213> ORGANISM: human

<400> SEQUENCE: 4

Asp Ile Asn Gly Lys Leu Phe Leu Pro Lys Tyr Ala Leu Ser Gln Asp
 1               5                  10                  15

Val Cys Thr Tyr Arg Asp Phe Ile Tyr Arg Thr Val Glu Ile Pro Gly
                20                  25                  30

Cys Pro Leu His Val Ala Pro Tyr Phe Ser Tyr Pro Val Ala Leu Ser
            35                  40                  45

Cys Lys Cys Gly Lys Cys Asn Thr Asp Tyr Ser Asp Cys Ile His Glu
        50                  55                  60

Ala Ile Lys Thr Asn Tyr Cys Thr Lys Pro Gln Lys Ser Tyr Leu Val
65                  70                  75                  80

Gly Phe Ser Val
```